United States Patent [19]

Wagner

[11] Patent Number: 5,302,374
[45] Date of Patent: Apr. 12, 1994

[54] ORAL HYGIENE SYSTEM

[75] Inventor: Eugene C. Wagner, Chappaqua, N.Y.

[73] Assignee: Dental Concepts Inc., Elmsford, N.Y.

[21] Appl. No.: 50,565

[22] Filed: Apr. 21, 1993

[51] Int. Cl.$^5$ .......................... A61K 7/16; A61K 7/18; A61K 7/20

[52] U.S. Cl. .......................... 424/52; 424/49; 424/53

[58] Field of Search ...................... 424/49-58

[56] References Cited

U.S. PATENT DOCUMENTS

| | | | |
|---|---|---|---|
| 4,405,599 | 9/1983 | Smigel, I | 424/53 |
| 4,522,805 | 6/1985 | Gordon | 424/52 |
| 4,528,180 | 7/1985 | Schaeffer | 424/52 |
| 4,603,045 | 7/1986 | Smigel, II | 424/52 |
| 4,687,663 | 7/1987 | Schaeffer | 424/52 |
| 4,690,776 | 9/1987 | Smigel, III | 252/315.3 |
| 4,776,500 | 10/1988 | Ford | 222/402.1 |
| 4,983,379 | 1/1991 | Schaeffer | 424/52 |
| 5,041,280 | 8/1991 | Smigel, IV | 424/52 |
| 5,084,268 | 1/1992 | Thaler, I | 424/53 |
| 5,085,853 | 2/1992 | Williams et al. | 424/53 |
| 5,122,365 | 6/1992 | Murayama | 424/49 |
| 5,165,424 | 11/1992 | Silverman | 128/861 |
| 5,171,564 | 12/1992 | Nathoo et al. | 424/53 |
| 5,208,010 | 5/1993 | Thaler, II | 424/53 |

*Primary Examiner*—Shep K. Rose
*Attorney, Agent, or Firm*—Natter & Natter

[57] ABSTRACT

A conventional toothpaste is dispensed on a toothbrush along with a quantity of an abrasive free dentifrice containing hydrogen peroxide as an active constituent. Abrasion constituents of the conventional toothpaste interact with the hydrogen peroxide constituent of the dentifrice to accelerate the breakdown of the hydrogen peroxide constituent and the release of active oxygen. The employment of corn starch as a base for the hydrogen peroxide dentifrice also results in a significant reduction in dentin abrasion levels as compared with the conventional toothpaste alone.

11 Claims, No Drawings

ORAL HYGIENE SYSTEM

BACKGROUND OF THE INVENTION

1. Field of the Invention

This invention relates generally to dentifrices and more particularly to a system employing a mixture of conventional toothpaste in combination with a dentifrice preparation having hydrogen peroxide as an active constituent.

2. Background History

The efficacy of peroxide compounds in oral hygiene has been long recognized. Such compounds have proven useful in the treatment of gingivitis, oral lesions, periodontitis, herpetic stomatitis and also in combatting plaque. Additionally, peroxide compounds have been utilized for oral cosmetic purposes such as tooth whitening. The release of active oxygen from a hydrogen peroxide dentifrice constituent in the oral cavity is believed to be primarily associated with the exposure of the hydrogen peroxide to the enzyme catalase.

Problems encountered with respect to providing stable shelf life for such dentifrices were addressed in U.S. Pat. No. 5,804,268 issued Jan. 28, 1992 to the assignee of the instant application.

While the abrasive free peroxide based dentifrice formulations disclosed in such patent have proven efficacious for routine oral hygiene and cosmetic purposes, Applicant has recognized the desirability of accelerating the breakdown of the hydrogen peroxide constituent and the release of oxygen within the oral cavity. Applicant has also recognized that in recent times, larger proportions of abrasives have been employed in conventional toothpastes. This has resulted in a concomitant increase in the potential for abrasion damage to tooth structure.

A need has been established for providing a system whereby efficacious cleansing of tooth surfaces can be achieved with reduced dentin abrasion levels.

SUMMARY OF THE INVENTION

In compendium, the invention comprises an oral hygiene system whereby a quantity of dentifrice comprising a blend of relatively abrasive free constituents including a corn starch base and hydrogen peroxide as an active ingredient is placed upon the bristles of a toothbrush along with a quantity of conventional toothpaste having from approximately 20% to 50% abrasive constituent comprising a metal salt.

The abrasive constituents of the conventional toothpaste function to accelerate the decomposition of the hydrogen peroxide constituent of the dentifrice while the peroxide dentifrice functions to reduce the dentin abrasion levels of the conventional toothpaste. The combined dentifrice and toothpaste synergistically function with enhanced deployment of active oxygen and with reduced dentin abrasion.

From the foregoing summary it will be appreciated that it is an aspect of the present invention to provide a system for oral hygiene which is not subject to the disadvantages of the background history aforementioned.

To provide a system for oral hygiene of the general character described which produces gentle cleansing of tooth surfaces while minimizing irritation and dentin abrasion otherwise encountered with the use of conventional toothpastes is another aspect of the present invention.

A feature of the present invention is to provide a system for oral hygiene of the general character described which achieves efficacious results in the treatment and prevention of gum disease.

A consideration of the present invention is to provide a system for oral hygiene of the general character described which provides enhanced generation of oxygen from a hydrogen peroxide dentifrice constituent within the oral cavity.

Another aspect of the present invention is to provide a system for oral hygiene of the general character described which is simple to practice.

To provide a system for oral hygiene of the general character described which enhances the flavor of a conventional toothpaste is another feature of the present invention.

Other aspects, features and considerations of the present invention in part will be obvious and in part will pointed out our hereinafter.

With these ends in view, the invention finds embodiment in the various combinations of elements, arrangements of constituents and series of steps by which the aspects, features and considerations aforementioned and certain other aspects, features and considerations are attained, all with reference to the following description of the preferred embodiments and the scope of which will be more particularly pointed out and indicated in the appended claims.

DESCRIPTION OF THE PREFERRED EMBODIMENTS

The present invention provides a system for oral hygiene whereby a dentifrice which includes hydrogen peroxide as its active constituent is placed in contact with a conventional toothpaste having, as an abrasive agent, between approximately 20% to 50% of a metal salt. The mixing of the peroxide containing dentifrice with the conventional toothpaste within the oral cavity during tooth brushing causes accelerated release of oxygen by interacting with the hydrogen peroxide constituent and/or by increasing the alkalinity level of the combined mixed formulation as compared with the pH level of the hydrogen peroxide containing dentifrice alone.

The hydrogen peroxide containing dentifrice may comprise a tooth whitening dentifrice as disclosed in U.S. Pat. No. 5,084,268, such as the commercially available hydrogen peroxide dentifrice sold under the registered trademark STAY-WHITE ®. STAY-WHITE ® dentifrice is a non-abrasive dentifrice comprising a blend of essentially 2% to 35% corn starch, which functions as a jelling agent, a thickener, a filler and a binder, from 5% to 30% sorbitol which functions as a humectant and sweetening agent, from 0.2% to 10% hydrogen peroxide, from 0.2% to 4% Carbomer 940 which comprises a gum and jelling agent, 0.1% to 2% flavor, from 0.2% to 2% sodium laurel sulfate, which functions as a foaming and surfactant agent, from 0% to 0.25% potassium sorbate which functions as a preservative, 0.1% to 0.25% sodium benzoate which functions as a preservative and deionized water in a sufficient quantity. Additionally, a water softening chelating agent such as EDTA (approximately 0.1%) may be employed.

In accordance with the invention, a ribbon or strip of the hydrogen peroxide containing dentifrice is extruded on the bristle ends of a toothbrush along with a equal volume ribbon or strip of conventional toothpaste. Depending upon the size of the toothbrush head and whether the dentifrice and toothpaste are deployed on top of one another or end to end, from approximately 1.3 to 2.5 grams of conventional toothpaste is dispensed and from 0.7 to 1.5 grams of peroxide dentifrice is dispensed.

Typical examples of toothpaste formulations which may be employed in conjunction with a dentifrice having hydrogen peroxide as its active constituent ingredient in the practice of the present invention are set forth in the following tables:

EXAMPLE 1

| Ingredient | Parts |
| --- | --- |
| Sorbitol and related Polyols | 62.0 |
| Hydrated Silica or Aluminum Hydroxide | 23.0 |
| Water | q.s. |
| Glycerin | 3.0 |
| SD Alcohol 38B | 2.0 |
| Sodium Lauryl Sulfate | 1.5 |
| Cellulose Gum | 1.0 |
| Sodium Monofluorophosphate | 0.7 |
| Flavor | .7 |
| Sodium Saccharin | 0.2 |
| Sodium Benzoate | 0.2 |
| Colorant | q.s. |

The abrasive constituent in such toothpaste formulation comprises Hydrated Silica or Aluminum Hydroxide.

A further example of a suitable toothpaste formulation for utilization in conjunction with the present invention is set forth in the following table:

EXAMPLE 2

| Ingredient | Parts |
| --- | --- |
| Water | q.s. |
| Hydrated Silica or Aluminum Hydroxide | 40.0 |
| Glycerin | 25.0 |
| Sorbitol | 15.0 |
| Tetrasodium Pyrophosphate | 5.0 |
| Sodium Lauryl Sulfate | 1.5 |
| Cellulose Gum | 1.2 |
| PEG-12 | 1.0 |
| PVM/MA Copolymer | 1.0 |
| Sodium Fluoride | 0.2 |
| Sodium Saccharin | 0.2 |
| Sodium Hydroxide | 0.1 |
| Flavor | .7 |
| Colorant | q.s. |

As with Example 1, the abrasive constituent in the above toothpaste formulation is Hydrated Silica. The Hydrated Silica contained therein is in a higher concentration than in Example 1. The toothpaste formulation of Example 2 utilizes a higher percentage of abrasive material, Hydrated Silica for the purpose of providing a tartar control or anti-tartar abrasive formulation. Additional constituents of such formulation which may provide anti-tartar characteristics include Tetrasodium Pyrophosphate and PVM/MA Copolymer.

A further suitable toothpaste formulation is set forth in the following table:

EXAMPLE 3

| Ingredient | Parts |
| --- | --- |
| Sorbitol | 33.0 |
| Hydrated Silica Aluminum Hydroxide | 24.0 |
| Water | q.s. |
| Glycerin | 10.0 |
| Tetrasodium Phosphate | 5.0 |
| Sodium Lauryl Sulfate | 1.5 |
| Cellulose Gum | 1.3 |
| Flavor | 0.7 |
| PEG-12 | 0.5 |
| Sodium Fluoride | 0.25 |
| Sodium Saccharin | 0.2 |
| Colorant | q.s. |

An additional suitable toothpaste formulation is set forth in the following table:

EXAMPLE 4

| Ingredient | Parts |
| --- | --- |
| Sorbitol | 40.0 |
| Calcium Carbonate | 30.0 |
| Water | q.s. |
| Hydrated Silica | 10.0 |
| Sodium Lauryl Sulfate | 1.5 |
| Cellulose Gum | 1.3 |
| Sodium Monofluorophosphate | 0.7 |
| Flavor | .7 |
| Calcium Carrageenan | 0.5 |
| PEG-8 | 0.5 |
| Titanium Dioxide | 0.2 |
| Sodium Saccharin | 0.2 |
| Sodium Benzoate | 0.2 |
| Colorant | q.s. |

It should be noted that the abrasive constituent in Example 4 comprises 30% Calcium Carbonate.

A further toothpaste formulation suitable for employment in conjunction with the present invention is set forth in the following table:

EXAMPLE 5

| Ingredient | Parts |
| --- | --- |
| Sorbitol | 30.0 |
| Water | q.s. |
| Hydrated Silica or Aluminum Hydroxide | 25.0 |
| Trisodium Phosphate | 5.0 |
| Sodium Lauryl Sulfate | 1.5 |
| Carbomer 956 | 1.0 |
| Xanthan Gum | 0.7 |
| Flavor | 0.7 |
| Sodium Fluoride | 0.2 |
| (.15% fluoride by volume) | |
| Sodium Phosphate | 0.2 |
| Sodium Saccharin | 0.2 |
| Titanium Dioxide | 0.2 |
| Colorant | q.s. |

A further toothpaste formulation suitable for employment in the present invention is set forth in the following table:

EXAMPLE 6

| Ingredient | Parts |
| --- | --- |
| Dicalcium Phosphate Dihydrate | 45.0 |
| Water | q.s. |
| Glycerin | 35.0 |
| Sodium Lauryl Sulfate | 1.5 |

-continued

| Ingredient | Parts |
|---|---|
| Cellulose Gum | 1.2 |
| Sodium Monofluorophosphate | 0.7 |
| Flavor | 0.75 |
| Sodium Benzoate | 0.2 |
| Tetrasodium Pyrophosphate | 0.2 |
| Sodium Saccharin | 0.2 |

An additional toothpaste formulation is set forth in the following table:

EXAMPLE 7

| Ingredient | Parts |
|---|---|
| Calcium Carbonate | 45.7 |
| Starch | 7.0 |
| Glycerol | 28.2 |
| Water | 14.4 |
| Sodium Benzoate | 2.2 |
| Flavoring | 1.3 |
| Sodium Lauryl Sulfate | 1.2 |

Examples of a suitable hydrogen peroxide containing dentifrice for use in conjunction with the present invention are set forth in U.S. Pat. No. 5,084,268 incorporated herein by reference. It should be appreciated however, that the system of the present invention will function with any extrudable dentifrice formulation having a hydrogen peroxide constituent and numerous formulations are commercially available.

Pursuant to the invention, equal volumes of peroxide containing dentifrice and conventional toothpaste are extruded onto the ends of bristles of a toothbrush and the toothbrush is inserted into the oral cavity with the user brushing teeth interdental spaces and gingival tissue in a normal fashion with conventional brush strokes. It has been found that the constituents of conventional toothpaste present an environment which accelerates the breakdown of the hydrogen peroxide constituent and the generation of active oxygen within the oral cavity. At least one factor involved in the mechanism involving the accelerated breakdown of the hydrogen peroxide constituent of the dentifrice is the fact that conventional toothpastes include pH elevating constituents and at elevated pH levels, hydrogen peroxide decomposes more readily.

It is believed that a major factor in the accelerated breakdown of the hydrogen peroxide constituent is the abrasive constituent of the conventional toothpaste. In many instances, the abrasive constituent of a conventional toothpaste comprises Hydrated Silica (Example 1, Example 2, Example 3 and Example 5). In other instances, the abrasive constituent comprises Calcium Carbonate (Example 4 and Example 7). While in other toothpaste formulations, the abrasive constituent comprises Dicalcium Phosphate Dihydrate (Example 6). These abrasive compounds comprise metal salts which reduce the peroxide to initiate the release of oxygen. Further conventional toothpaste constituents which are believed to accelerate the decomposition of Hydrogen Peroxide include Sodium Fluoride, Sodium Monofluorophospate, Tetrasodium Pyrophosphate, Tetrasodium Phosphate, Titanium Dioxide, Cellulose Gum, Sodium Hydroxide, Trisodium Phosphate and Sodium Phosphate.

It has also been observed that brushing with a mixture of both conventional toothpaste and a dentifrice having a Hydrogen Peroxide constituent results in enhancement of the flavoring of the conventional toothpaste. While the exact mechanism of such enhancement is unknown, it is believed that the generation of free oxygen within the oral cavity includes, among its beneficial effects, the enhancement of taste sensitivity.

An additional beneficial result of practicing the method of the present invention results in reduced dentin abrasion levels. A laboratory study has been conducted to determine the relative abrasiveness of a mixture containing equal portions of STAY-WHITE ® dentifrice and a toothpaste sold under the trademark COLGATE Tartar Control. The test comprised brushing dentin specimens for 1,500 strokes using a slurry consisting of 25 gm Colgate Tartar Control in 40 ml water, a further slurry consisting of a mixture of 12.5 gm STAY-WHITE ® peroxide dentifrice and 12.5 gm Colgate Tartar Control in 40 ml water and a reference slurry consisting of 10 gm ADA reference abrasive in 50 ml of 0.5% CMC glycerin solution.

The ADA reference abrasive was assigned a value of 100 and its ratio to the test material was calculated.

The results of such test are reported in the table below:

TABLE

| Specimen | Dentin Abrasion Level Colgate Tartar Control | Dentin Abrasion Level Stay-White + Colgate Tartar Control |
|---|---|---|
| 1 | 92.27 | 73.51 |
| 2 | 94.04 | 68.86 |
| 3 | 124.70 | 78.98 |
| 4 | 90.97 | 71.66 |
| 5 | 106.84 | 55.06 |
| 6 | 122.53 | 66.56 |
| 7 | 105.66 | 53.88 |
| 8 | 95.57 | 68.20 |

From the results of such test it was concluded that when mixed in equal proportions, the combination of STAY-WHITE ® and Colgate Tartar Control toothpaste was significantly less abrasive to human dentin than utilizing Colgate Tartar Control toothpaste alone.

Thus, it will be seen that there is provided a oral hygiene system which achieves the various aspects, features and considerations of the present invention and which is well suited to meet the conditions of practical usage.

Since various possible embodiments might be made of the invention described herein without departing from the spirit of same, and various changes might be made in the exemplary embodiments set forth, it should be understood that all matters herein described are to be interpreted as illustrative, rather than in a limiting sense.

Having thus described the invention, there is claimed as new and desired to be secured by Letters Patent:

1. A method of cleansing tooth surfaces while reducing dentin abrasion which occurs during tooth brushing with a conventional abrasive-containing toothpaste, which comprises the steps of:
   (a) providing a sufficient amount of a conventional toothpaste containing from 20% to 50% by weight of an abrasive agent selected from the group consisting of hydrated silica, aluminum hydroxide, calcium carbonate, and dicalcium phosphate dihydrate;
   (b) providing a sufficient amount of non-abrasive, aqueous, homogeneously dispersed dentifrice having a toothpaste consistency and comprising from 0.2% to 10% by weight of hydrogen peroxide, from 0.2% to 4% by weight of Carbomer 940 gelling agent, from 2% to 35% by weight of corn starch filler, and from 0.2% to 2% by weight of surfactant and foaming agent, based upon the weight of the total dentifrice;

(c) admixing the conventional toothpaste from step (a) with the dentifrice from step (b) to accelerate the release of oxygen from the dentifrice; and (d) brushing tooth surfaces with the admixture from step (c).

2. The method of claim 1, wherein the volume amount of conventional toothpaste in step (a) is substantially equal to the volume amount of dentifrice in step (b).

3. The method of claim 1, wherein the mixture in step (c) comprises from 1.3 to 2.5 grams of conventional toothpaste and from 0.7 to 1.5 grams of dentifrice.

4. The method of claim 1, wherein the conventional toothpaste also contains one or more compounds selected from the group consisting of sodium fluoride, sodium monofluorophosphate, tetrasodium pyrophosphate, tetrasodium phosphate, titanium dioxide, cellulose gum, sodium hydroxide, trisodium phosphate, and sodium phosphate, in an amount sufficient to accelerate decomposition of the hydrogen peroxide.

5. The method of claim 1, wherein step (c) includes the step of providing a toothbrush and dispensing substantially equal volumes of dentifrice and toothpaste on the bristles of the toothbrush, and step (d) includes the step of placing the bristles of the toothbrush in the oral cavity and brushing tooth and gum surfaces.

6. A method of cleansing tooth surfaces while reducing dentin abrasion which occurs during tooth brushing with a conventional abrasive-containing toothpaste, which comprises the steps of:

(a) admixing an amount of conventional abrasive-containing toothpaste containing from 20% to 50% by weight of an abrasive agent selected from the group consisting of hydrated silica, aluminum hydroxide, calcium carbonate, and dicalcium phosphate dihydrate with an amount of a non-abrasive, aqueous, homogeneously dispersed dentifrice having a toothpaste consistency and comprising from 0.2% to 10% by weight of hydrogen peroxide, from 0.25% to 4% by weight of Carbomer 940 gelling agent, from 2% to 35% by weight of corn starch filler, and from 0.2% to 2% by weight of surfactant and foaming agent, based upon the weight of the total dentifrice; and (b) brushing tooth surfaces with the admixture from step (a).

7. The method of claim 6, wherein the step (a) the volume amount of conventional toothpaste is substantially equal to the volume amount of dentifrice.

8. The method of claim 6, wherein the mixture in step (c) comprises from 1.3 to 2.5 grams of conventional toothpaste and from 0.7 to 1.5 grams of dentifrice.

9. The method of claim 6, wherein the conventional toothpaste also contains one or more compounds selected from the group consisting of sodium fluoride, sodium monofluorophosphate, tetrasodium pyrophosphate, tetrasodium phosphate, titanium dioxide, cellulose gum, sodium hydroxide, trisodium phosphate, and sodium phosphate, in an amount sufficient to accelerate decomposition of the hydrogen peroxide.

10. The method of claim 6, wherein step (c) includes the step of providing a toothbrush and dispensing substantially equal volumes of dentifrice and toothpaste on the bristles of the toothbrush, and step (d) includes the step of placing the bristles of the toothbrush in the oral cavity and brushing tooth and gum surfaces.

11. A dentifrice-toothpaste mixture suitable for instantaneous employment in an oral hygiene program for the treatment of tooth surfaces and gum tissue, the mixture comprising (a) a non-abrasive, aqueous, homogeneously dispersed dentifrice having a toothpaste consistency and comprising from 0.2% to 10% by weight of hydrogen peroxide, from 0.25% to 4% by weight of Carbomer 940 gelling agent, from 2% to 35% by weight of corn starch filler, and from 0.2% to 2% by weight of surfactant and foaming agent, based upon the weight of the total dentifrice, and (b) a conventional abrasive-containing toothpaste containing from 20% to 50% by weight of an abrasive agent selected from the group consisting of hydrated silica, aluminum hydroxide, calcium carbonate, and dicalcium phosphate dihydrate, the abrasive agent serving to accelerate the decomposition of the hydrogen peroxide in the dentifrice upon formation of the mixture.

* * * * *